United States Patent [19]

Calhoun et al.

[11] Patent Number: 5,212,992
[45] Date of Patent: May 25, 1993

[54] CAPACITIVE PROBE SENSOR WITH REDUCED EFFECTIVE STRAY CAPACITANCE

[75] Inventors: Jeffrey Calhoun, Peekskill; Stanimir T. Zupanski, Bedford, both of N.Y.

[73] Assignee: Medical Laboratory Automation, Inc., Pleasantville, N.Y.

[21] Appl. No.: 715,434

[22] Filed: Jun. 14, 1991

[51] Int. Cl.$^5$ .................................................. B01L 3/02
[52] U.S. Cl. .................................... 73/864.01; 324/690
[58] Field of Search ............ 73/864.01, 304 C, 864.24; 324/663, 690, 671, 672, 673, 674, 658, 661; 340/620

[56] References Cited

U.S. PATENT DOCUMENTS 4,818,492 4/1989 Shimizu ........................ 73/864.24 X

*Primary Examiner*—Jerry W. Myracle
*Attorney, Agent, or Firm*—Wolf, Greenfield & Sacks

[57] ABSTRACT

A capacative probe is provided which has reduced effective stray capacitance and is thus able to accurately detect probe contact with a conducting fluid with small fluid volumes. Effective stray capacitance is reduced by dividing stray capacitance sources into two or more sources, by reducing the capacitance value of each of the divided stray capacitance sources to a value which is substantially less than the capacitance difference which occurs as a result of probe contact with the fluid and by connecting at least selected ones of the divided stray capacitance sources in series to further reduce effective stray capacitance. The capacitance value of the stray capacitances are reduced by providing a gap in a conducting tube covering the probe aspirating tube, which gap isolates conductive elements of the probe from the probe tip potential, thus reducing or eliminating the potential across various stray capacitance sources (and thus reducing or eliminating such sources) and also results in reduced plate sizes for such stray capacitance sources. A capacitance across the gap, which may be of a controlled small value, is also in series with selected stray capacitance sources, further reducing the effective stray capacitance of the probe.

12 Claims, 7 Drawing Sheets

CAPACITIVE PROBE SENSOR WITH REDUCED EFFECTIVE STRAY CAPACITANCE

FIELD OF THE INVENTION

This invention relates to an improved capacitve probe for accurately detecting contact of the probe tip with a conductive liquid, including extremely small volumes of the liquid. In particular, it pertains to a capacitance sensor with greatly reduced stray capacitance, thereby increasing the sensitivity of the probe to liquid contact.

BACKGROUND OF THE INVENTION

An apparatus commonly used in biomedical and analytical applications is a probe for aspirating a liquid from a container. The container is often a cuvette which is transported to an aspirating station where the probe is electromechanically lowered into the liquid and a syringe pump turned on to take up a measured amount of the liquid. In such applications, it is important that the control system know when the probe touches the surface of the liquid, so the downward motion can be automatically stopped and the syringe pump turned on. It is desirable that such determination be made electronically. Since, most liquids of interest (e.g., electrolytes, blood, plasma, water and the like) are electrically conductive, they can function as one plate of a capacitor, with the cuvette, test tube or other liquid receptical (hereinafter "tube") as a dialectric and system ground immediately outside the tube. Thus, measuring the capacitance at the tip of the probe is an excellent technique for determining when the probe is above versus when it has made contact with the surface of the liquid sample.

The aspirating tube is usually made of flexible plastic material with a small bore hole running the length thereof. The aspirating tube is placed in a hollow metal tube that protects the plastic tube and gives it rigidity. This concentric arrangement, the non conducting plastic aspirating tube within a metal tube, extends within a cylindrical metal housing which is coupled to a gear drive or other precision motion drive that mechanically drives the probe into and out of the liquid sample. Both the housing that holds the aspirating tube rigid and the driven outer housing are typically made of stainless steel.

In the above arrangement the tip of the metal rigidizing tube is used as the capacitance measuring point. The tip is typically connected to an oscillator the frequency of which changes with changes in capacitance at the tip. When the probe is not in the liquid, the oscillator frequency is due almost entirely to the "parasitic" or "stray" capacitance at the tip. When the probe is in the liquid, it senses the capacitance of the liquid to ground through the tube which changes the frequency of oscillation.

The capacitance of the liquid to ground depends upon the contact area between the liquid and the tube, which will be small for small volumes of liquid. Accordingly, the capacitance for small volumes of liquid may be small compared to the "stray" capacitance. For at least one prior art probe, the stray capacitance is as large or larger than the capacitance of the liquid to ground. Furthermore, because the motion drive causes slight shaking and vibration of the probe as it is driven down toward the liquid, the value of the stray capacitance in that prior art probe is unstable and subject to frequent changes, which changes can be relatively large.

Another potential source of stray capacitance involves the asperated ionic fluid functioning as one plate. Since this capacitance can vary with the type of fluid in the probe (not being present, for example, if the fluid in the probe is non-ionic or if there are air bubbles in the probe separating fluid layers), with vibration or other movement of the fluid and with other factors, this stray capacitance is both not well-defined and unstable. Under worst case conditions, it may also be relatively large.

These stray capacitances make detection difficult, since, to reliably measure changes in capacitance due to the probe entering the liquid, all other capacitors in the circuit must either be small compared to it, or invariant so they can be differentially eliminated. Ideally, such stray capacitances are both small and invariant. The prior art transducer meets neither of these criteria.

SUMMARY OF THE INVENTION

Therefore it is an object of this invention to provide a capacitive liquid detection transducer that electronically detects when the probe is in the liquid with greatly reduced stray capacitance at the probe.

It is another object of this invention to provide a capacitive liquid detection transducer with enhanced ability to detect contact with small volumes of liquid.

Still another object of the invention is to provide a capacitive liquid detection transducer, the stray capacitance of which is at a value which is small compared to the capacitance change caused by the probe entering the liquid, and the variation in which as a result of vibrations or the like are even smaller.

It is another object of this invention to provide a capacitive transducer with a sensor that is electrically isolated from its supporting structure.

This invention recognizes that the unwanted "stray" or "parasitic" capacitance of the prior art transducer: a) is mainly due to the capacitance between the long rigidizing metal tube and the outer housing; b) is large; and c) is given to rapid changes in value for even small vibrations of the tube; the invention overcomes these problems by mechanically partitioning the rigidizing tube into two or more sections. Adjacent sections of the partitioned tube are spaced apart by an air gap, each section thus being capacitively coupled to an adjacent section across the intervening gap. For example, separating the rigidizing tube into two sections means that the upper probe tube is capacitively coupled to the lower probe tube across the air gap between them. The gap capacitor is relatively controllable and can be made small by providing a sufficiently large gap. The geometry also splits the sources of stray capacitance, thus reducing their value, and electrically isolates some of the stray capacitance plates to further reduce o eliminate such stray capacitance. The geometry also puts any remaining stray capacitance in series with a capacitance which may be controlled by the gap, or otherwise, to be of small value. Therefore, by virtue of the well known fact that the resultant value of two capacitors in series is smaller than the smaller of the two, the effective stray capacitance may be reduced to near negligible levels. However, since the capacitance at the tip when the probe touches liquid is not reduced, there is a large, easily detectable capacitance change when the probe touches liquid, even for small liquid volumes

DETAILED DESCRIPTION OF THE INVENTION

This invention pertains to an improved capacitive liquid detection probe with increased sensitivity including sensing extremely small volumes of liquid. The probe of the invention is designed to eliminate or reduce to negligible levels the stray or parasitic capacitance seen at the tip of the probe be electrically isolating the tip from the remainder of the probe.

In particular, this invention pertains to liquid aspirating probes which may, for example, be used in automated biomedical and analytical applications. The liquids aspirated by the probe of this invention are electrically conductive ionic liquids or electrolytes. The term "liquid" used herein is meant to exclude non ionic fluids such as distilled water.

Figure 1:
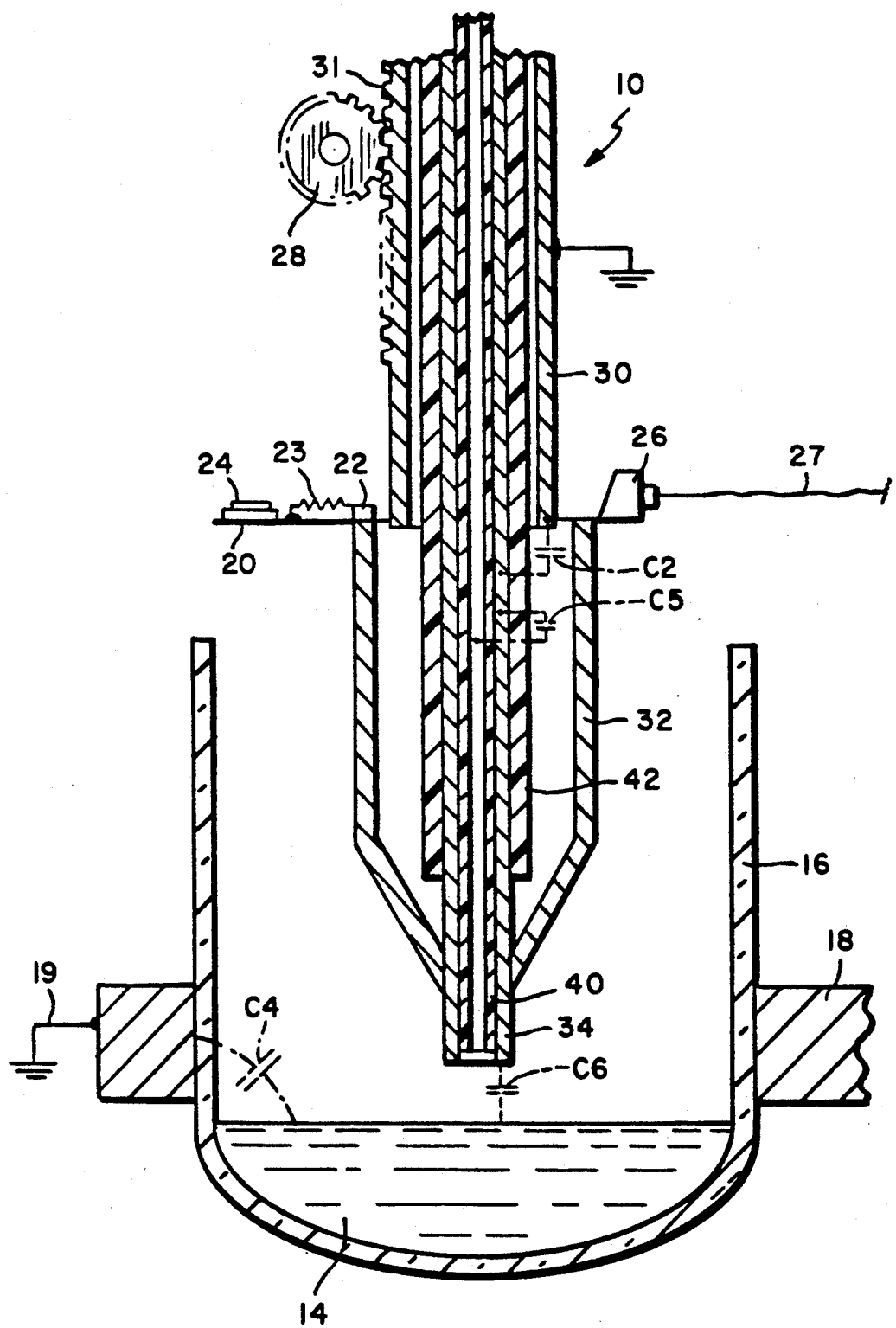
FIG. 1 is a cross sectional side view of a prior art liquid aspirator probe and capacitive transducer with the probe is above the liquid sample, the the major parasitic and other capacitances, for this probe also being shown.

FIG. 1 illustrates the structure of a prior art liquid aspirating probe 10 that incorporates a capacitive sensor. A liquid aspiration tube 40 is connected at one end to a syringe pump (not shown) and has its other end pointed toward the liquid 14. The aspirating tube 40 is housed within metal rigidizing tube 34. The tip of tube 34 and the tip of aspirating tube 40 will become immersed in the liquid as the probe is lowered, the tip of tube 34 sensing the capacitance of the liquid through the liquid containing tube to ground when it is immersed in the liquid.

A lower outer tube 32 is in pressure contact at its lower end with tube 34, and point 22 at the other end thereof is connected through resistor 23 to capacitive sensing circuit 24. Circuit 24, on a printed circuit board (PCB) 20, measures the capacitance at the tip of tube 34 and communicates that information to the remainder of the system via connector 26 and cable 27. Cable 27 also communicates power and ground to the PCB. The lower outer housing 32 is supported from PCB 20.

PCB 20 is in turn supported by an upper outer housing 30. Housing 30 is also constructed of a metal such as stainless steel or other suitable material, and includes an integral gear rack 31 that can be engaged by a worm gear or rotary gear 28 to drive the probe assembly 10 into and out of the liquid sample. Inner rigidizing tube 34 is electrically isolated from upper outer housing 30 by a plastic liner 42. This is required since housing 30 can be grounded to system ground which would short out the sensor at the tip of tube 34.

The sample liquid 14 is in a cuvette, glass test tube or other collection tube 16. Tube 16 is placed in and retained by a tube holder 18. A section of the outside of the tube is grounded by contact plate 19 which is in tube holder 18 specifically to make positive ground contact with one side of tube 16.

FIG. 1 shows the prior art probe 10 placed above the surface of the liquid sample into which it is being lowered. In this configuration, the capacitance to ground at the tip of the probe is mainly due to a) stray capacitor C2 between the rigidizing tube 34 and the outer upper housing 30; b) stray capacitance C5 between ionic fluid in tube 40 and rigidizing tube 34; and c) capacitor C6, between the tip of the probe and the liquid 14, in series with capacitor C4, between the liquid 14 and ground 19. Capacitor C6 is very small, (i.e., approximately 0.1 pf when the probe is close to the fluid surface) largely because the area at the tip of the probe is very small and air is a poor dialectric. Consequently, the series combination of capacitances C6 and C4, which is smaller than capacitor C6, is virtually negligible.

It should at this point be noted that while various stray and other capacitances are shown as discrete components in the figures, this is done for purposes of illustration only, the capacitances generally being distributed capacitances. For example, capacitance C2 occurs over the entire adjacent portion of housing 30 and tube 34.

Before the probe enters the liquid, the series combination of capacitors C2 and C5 is the dominant capacitance at the probe. Capacitor C2 can be of the order of 40–50 pf, which is equal to or larger than capacitance C4, the capacitance of the liquid sample to the ground contact on the outside of the cuvette. Capacitor C4 is usually between 10 pf and 50 pf, the specific value for C4 being a function of fluid depth (fluid depth controlling plate size).

Stray capacitor C5 in series with capacitor C2 may vary widely and unpredictably, making any preset compensation for stray capacitance difficult. Typically, an aspirating probe such as the probe 10 initially has a non-ionic wash fluid in it. Under these conditions, C5 might not exist and could be ignored. The potential at the fluid may also vary widely, depending on the potential at the pump (not shown) for the fluid. However, since there is typically some air in the tube between the pump and probe 10 and at least some of the fluid in the intervening space would typically be a non ionic fluid or a fluid with very poor conductivity such as water, the potential of the fluid in the tube would typically be at or near ground.

Further, in operation, the probe may aspirate two or more samples, for example a sample of blood and a sample of a dilutant, each of which samples may or may not be ionic, and each of which samples is separated by a small air bubble. Thus, the potential and conductivity of the fluid in the tube may vary substantially with time as the probe is being utilized. Movement of the fluid in tube 42 as the probe is being positioned and repositioned may cause further variations in stray capacitance C5. Capacitance C2 is also both large and unstable. Not only is it 40–50 pf, but it changes abruptly due to vibration of outer housing 30 and the associated vibration of the dielectric plastic lining 42.

Thus, the series combination of capcitances C2 and C5 may have widely varying capacitance values due primarily to variations in the value of capacitance C5, and both capacitances C2 and C5 may be unstable due to vibration or other movement. Therefore, since the sensor detects the point at which the probe enters the liquid by detecting the transition from what is primarily the stray capacitance (C2, C5) to what is a value dependent on capacitance C4 in parallel with the stray capacitances, the variances and instability in the stray capacitances makes such a determination difficult. In particular, when the probe enters the liquid, capacitances C5 and C6 disappear. Capacitance C5 disappears since the positive potential from tube 34 flows through the ionic fluid 14 and into the fluid in tube 42, bringing the two plates of capacitor C5 to substantially the same potential. Air in tube 42 between samples may prevent capacitance C5 from being completely shorted out when probe 10 is in liquid 14. However, the effect of capacitance C5 on the circuit may still be substantially reduced when the probe enters the liquid in ways which are difficult to predict. Capacitance C6 disappears because its dielectric disappears. Thus, the only capacitances remaining in the circuit at this time are the parallel combination of stray capacitance C2 and capacitance C4. The difference in this value from the value of the stray capacitance before the probe enters the fluid may be little different from the changes discussed above which occur in stray capacitance.

Accordingly, the prior art probe has difficulty differentiating between the probe making contact with the liquid and spurious capacitance changes due to vibration, movement or changes in the fluid in tube 42.

Figure 2:
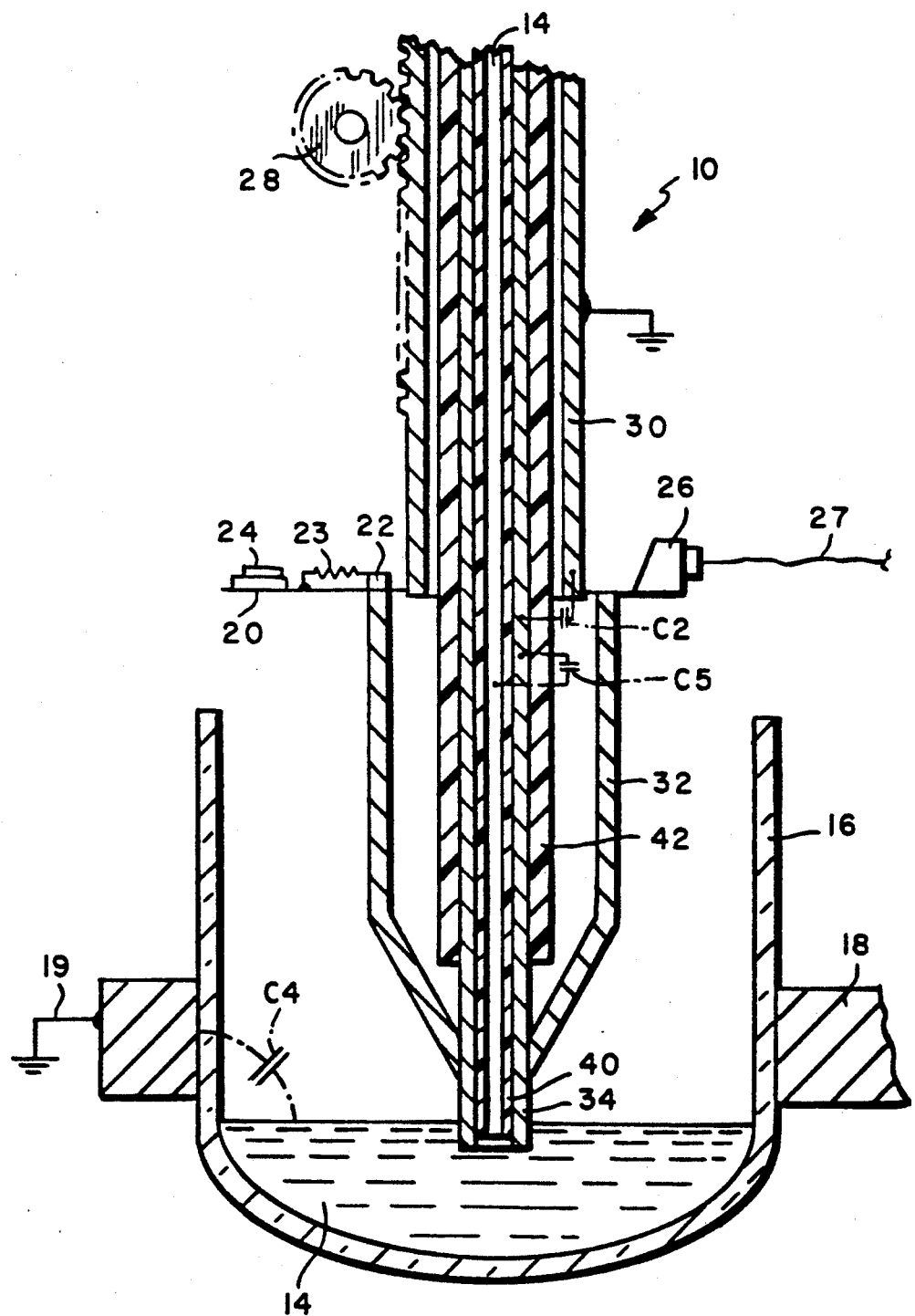
FIG. 2 is a cross sectional side view of the liquid aspirator and capacitive probe transducer of this invention showing the probe is above the liquid sample, and showing the major capacitances.

Referring to FIG. 2, the probe 11 of the preferred embodiment of the invention solves the problem presented by the large unstable stray capacitance C2 and unpredictable stray capacitance C5. This embodiment is similar to probe 10 of FIG. 1 except that the tube 34 of FIG. 1 is divided into two sections 34a and 34b, separated by an air gap 35. The two sections of the tube are firmly held a fixed distance apart by plastic tube or sleeve 42 which also electrically isolates the sections. The capacitor C1 between tube sections 34a and 34b may be kept small by controlling the size of air gap 35. For a preferred embodiment, gap 35 is approximately 0.25 inches. The plastic tubing 42 holding the tube sections firmly assures reasonable stability for the capacitance of capacitor C1.

FIG. 2 also illustrates the capacitance at the probe before the probe enters the liquid. Capacitor C1 between tube sections 34a and 34b is a fabricated air gap capacitor of this invention. Capacitor C5 is divided into two separate capacitors in parallel, capacitor C5a and C5b, as is stray capacitor C2 which is divided into separate stray capacitors, C2a and C2b. Since tube section 34b is substantially isolated from housing 32 containing positive potential, this tube has substantially no potential applied thereto. Therefore, there is little or no potential across capacitors C2b and C5b and these capacitors are basically eliminated from the circuit. The distance between housing 30 and tube 32a is large enough so that capacitor C2a is relatively small. Capacitors C1 and C5a are also small. Further, capacitor C5a is in series with negligible capacitor C2b. Since it is well understood by those practiced in the art that, when two capacitors are in series, they have an equivalent capacitance that is smaller than the smaller of the two capacitances, the effective capacitance of probe 11 may be made as small as is required to effectively determine contact with the fluid. For a preferred embodiment, the stray capacitance is approximately 1 pf.

When probe 11 touches fluid, capacitor C6 is eliminated and capacitor C4 is in parallel with what is effectively the parallel combination of capacitor C5a and capacitor C1. However, since the positive potential from tube 34a is applied to the fluid, the potentials on both plates of capacitor C5a are substantially identical, basically eliminating this capacitor from the circuit. Thus, the circuit is basically capacitors C1 and C4 in parallel when the probe is in the liquid. Since capacitor C1 can be made very small, in the order of 1 pf, even relatively small values of C4 which occur when the fluid in tube 16 is relatively low, for example 10 pf, are still substantially greater than C1 and easily detected.

The reduction in stray capacitance when the probe is out of liquid, from 40-50 pf to less than 1 pf, has at least two positive effects. The first has been discussed above in that it permits small liquid volumes to be more easily detected, thus increasing the sensitivity of the probe. Second, since C1 is relatively stable, variations in the capacitance of, for example, capacitor C5a, or any other stray capacitor, due to vibration, fluid movement, or any other cause, are of small absolute magnitude, such variations do not result in spurious detection. Even changes in C1 itself would be only a fraction of 1 pf and therefore would not result in spurious detection. A system with substantially enhanced sensitivity and stability is thus provided.

Figure 3:
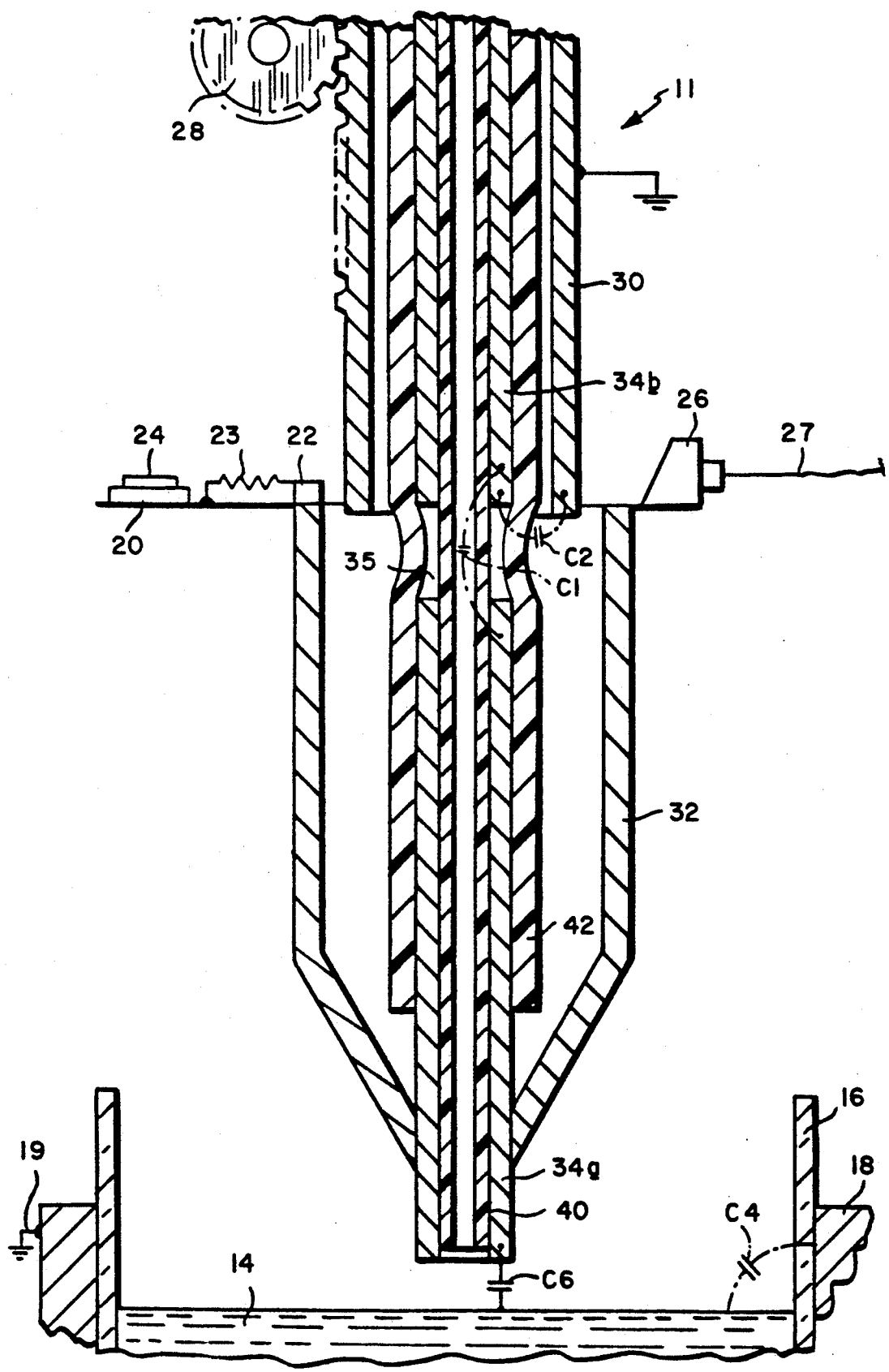
FIG. 3 is a schematic diagram of the capacitance sensing circuit of this invention.
Figure 4:
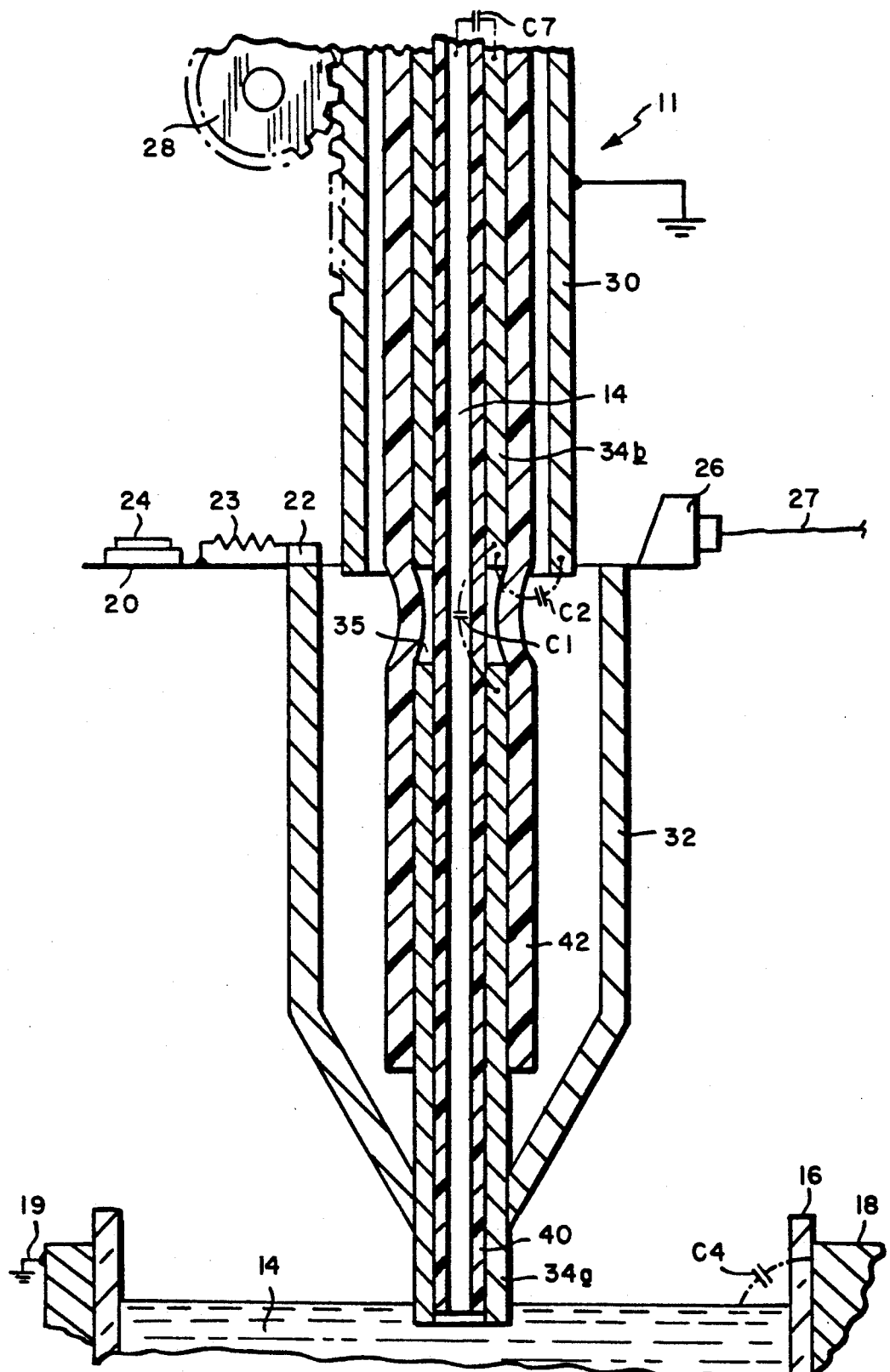
FIG. 4 is a block diagram of the liquid sensing system of this invention.
Figure 5:
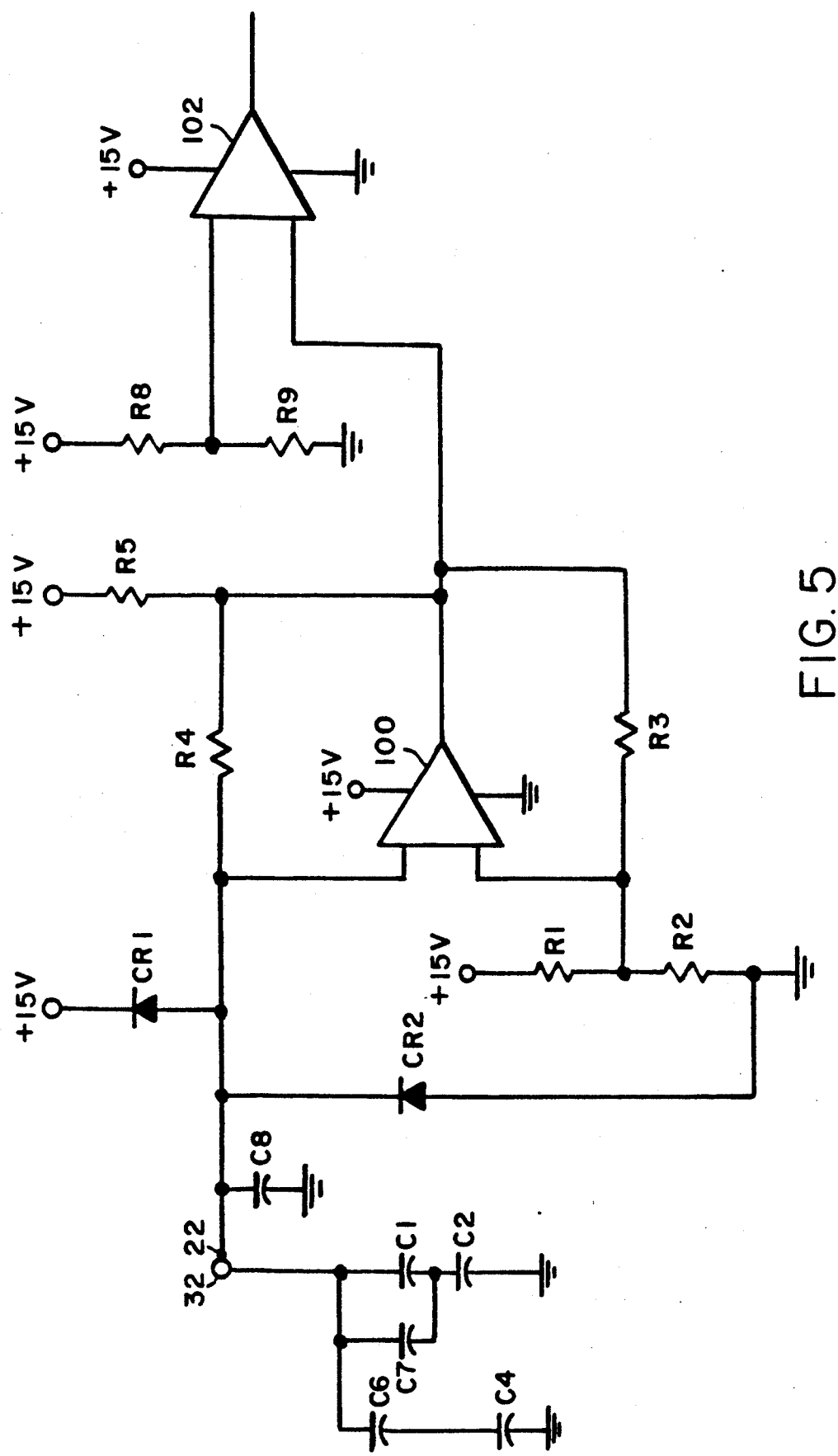
FIG. 5 is a cross-sectional side view of the aspirating/transducer probe of this invention with the rigidizing tube divided into three sections.

FIG. 5 is a schematic diagram of the capacitance sensing circuit of this invention. Point 22 of FIGS. 3 and 4 is schematically shown as contact point 22 o circle 32, which represents the outer lower housing 32 in FIGS. 2. To the right of circle 32 in FIG. 3 is the sensor circuit and the stray capacitance C8 on the PCB from the sensing point to ground. To the left of circle 32 in FIG. 3 are the capacitances seen by the tip of the probe of this invention. Capacitor C1 and the split stray the capacitors C2a, C2b, C5a and C5b are the capacitors unique to the probe of this invention.

From FIG. 3 it is see that there are four parallel capacitive paths between the detector which is a positive potential source and ground, two of which paths include capacitor C2b. Of the three stray capacitance paths, one of these paths is through capacitor C2a which, as a result of the spacing between tubes 34a and 34b, can be made very small, less than 1 pf. The second path is through capacitors C1 and C2b. Capacitor C1 can also be made small, with a magnitude of less than 1 pf, and since there is virtually no potential difference across capacitor C2b, this capacitor is virtually eliminated from the circuit. The third stray capacitance path is through capacitors C5a, C5b and C2b. Since capacitors C5a and C2b are substantially eliminated from the circuit, this leg is made up primarily of capacitor C5a. This capacitance would also be relatively small and the combined capacitance of C5a and C5b in series with C5b having negligible capacitance, would also be very small. The combined capacitance of the three parallel stray paths can thus be maintained in the order of 1 pf.

Similarly, capacitance C6, the capacitance from the tip of the probe to the liquid, is very small (e.g., 0.1 pf) and guarantees that capacitance C4 is effectively out of the circuit when the probe is above the surface of the liquid. Thus, the capacitance at point 22 when the probe is out of the liquid is in the order of 1 pf. When the probe touches the liquid, capacitance C6 is shorted out, and for reasons previously discussed, capacitance C4 dominates the capacitance at point 22. Since this capacitance can be in the order of 10 pf to 50 pf, the capacitance change when the probe touches the liquid is easily detected.

To the right of circle 32 is the electronic sensing circuit. Capacitance C8 is the stray capacitance at point 22 within the PCB. Comparator 100 is an oscillator whose frequency is directly proportional to the total capacitance at point 22. Resistor R4 forms an RC network that alternately charges the probe capacitance to +15 volts and then discharges it to ground, as comparator 100 alternately saturates to +15 volts and then to ground. In order to keep the sensitivity of the circuit high, R4 should be large and the capacitance at point 22 should be small. In a preferred embodiment, the frequency of oscillator 100 is set to about 250 kHz for the condition when the probe is out of the liquid. Once the probe touches the liquid, the frequency of oscillation is reduced by an amount that depends upon the value of capacitor C4. Comparator 102 is a buffer that enables the oscillating signal to be driven over cable 27 to the motion control system.

Figure 6:
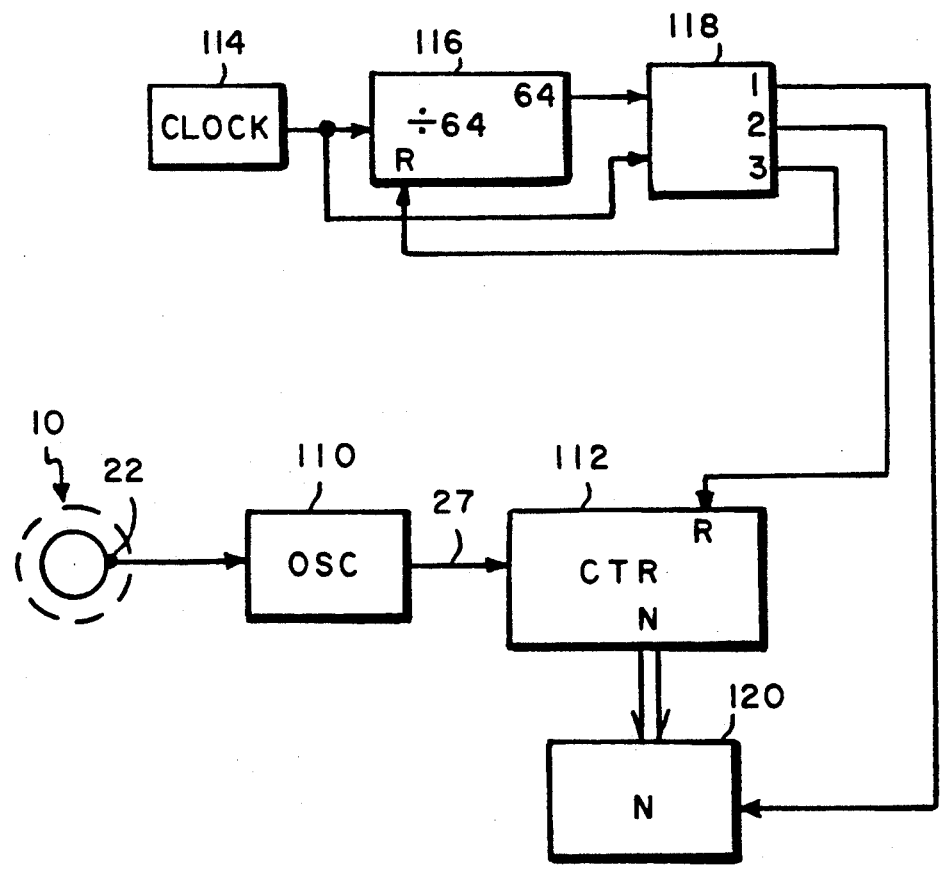

FIG. 6 is a block diagram of the preferred embodiment of the motion control system. The block diagram shows that oscillator 110 is coupled to probe 11 at point 22. Oscillator 110 communicates with the rest of the system over cable 27.

The frequency from oscillator 110 is divided by sixty-four in a binary counter 112 and used as a gating Set-Reset function to count N number of cycles of the 1 MHz clock 114. The value of counter 116 is strobed into register $R_1$ and the next reading into register $R_2$. The two values are compared and if the difference between $N_1$ and $N_2$ is greater than a predetermined value, for example five counts, this indicates that the probe has contacted the liquid.

This process is repeated for each step of the probe toward the liquid. For example, in a preferred embodiment, this operation is repeated every 2 mili-seconds for a Step Rate of 500 Steps/Sec. The value that the counter reaches in each gating interval is a measure of capacitance at point 22. When N is high the capacitance at point 22 is high. When the probe enters liquid, N will increase so that the difference $N_2 - N_1 > 5$ counts.

After detecting liquid, the control electronics moves the probe a pre determined number of steps down into the liquid in order to aspirate. During aspiration, the probe may be moved further down into liquid if necessary to access the full volume. After aspiration, the system re checks the sensing circuit to make sure probe 11 was submerged in liquid during the entire aspiration. The probe then moves to the next location, and dispenses the liquid and the process continues under computer control.

Figure 7:
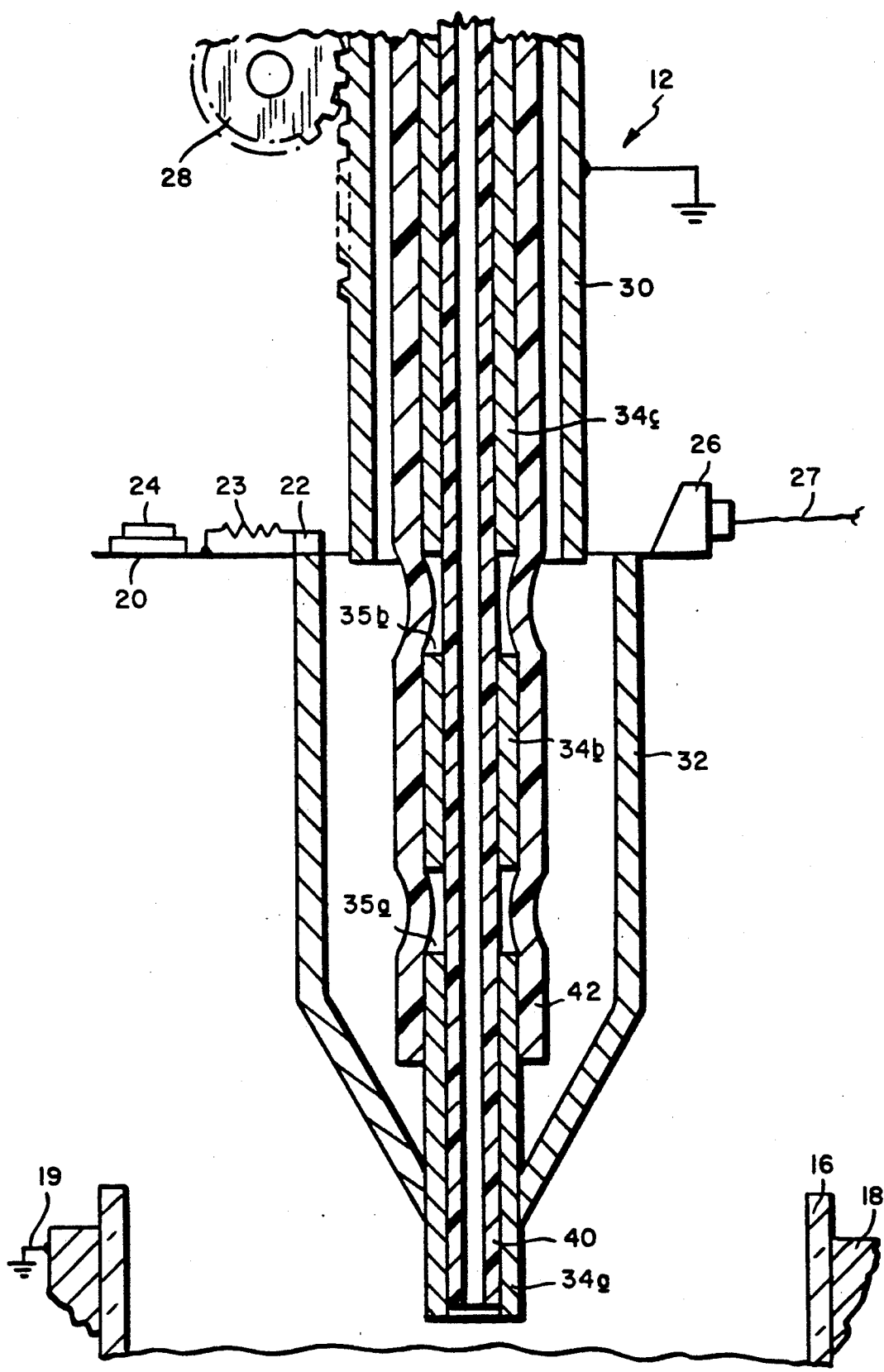

FIG. 7 shows probe 12 of this invention with probe tube 34 divided into three sections 34a, 34b and 34c. Capacitors C1a and C1b are formed between sections 34a/34b and 34b/34c, respectively. These capacitors are in series with each other and would replace capacitor C1 in the circuit of FIG. 3. Dividing tube 34 in three sections would also result in a further fragmenting of stray capacitors C2 and C5.

While particular probe structures and particular sensing circuitry have been described above, other structure and/or circuitry performing the same or equivalent functions might also be utilized. Thus, while preferred embodiments of the invention have been set forth above, it is to be understood that this is for the purpose of illustrating the invention by way of example only, and should not be construed as limiting the scope of the invention, since it is apparent that the foregoing and other changes can be made to the disclosed embodiments by those skilled in the art to suit particular applications. Accordingly, the invention is defined not by the illustrative embodiment, but only by the following claims and their equivalents.

What is claimed is:

1. In a probe for aspirating an ionic liquid sample and for sensing a capacitance difference at the probe tip when it is not in contact with the liquid and when it is in contact with the liquid, apparatus for providing an effective stray capacitance from stray capacitance source which is substantially less than said capacitance difference comprising:

means for dividing stray capacitance sources into at least two sources; and means for reducing the capacitance value of each divided stray capacitance source to a value substantially less than said capacitive difference.

2. Apparatus as claimed in claim 1 including means for connecting at least selected ones of the divided stray capacitance sources in series.

3. Apparatus as claimed in claim 1 including means for creating at least one additional source of stray capacitance which is substantially smaller than said capacitance difference and is connected in series with at least one of said divided stray capacitance sources.

4. Apparatus as claimed in claim 1 wherein said probe includes an aspirating tube of an insulating material extending the length of said probe, and said apparatus includes at least two conductive tube sections coaxial with said aspirating tube, a first of said sections extending from the probe tip, covering a selected portion of the aspirating tube which is substantially less than all of said aspirating tube and having a selected potential applied thereto, a second section being spaced by a selected gap from said first section, covering a portion of said aspirating tube not covered by said first section, and not having the selected potential applied thereto, whereby there is a potential difference between said sections.

5. Apparatus as claimed in claim 4 including a cover tube of an insulating material covering at least the adjacent portions of the first and second sections, the cover tube in conjunction with the aspirating tube maintaining said selected gap.

6. Apparatus as claimed in claim 4 wherein said stray capacitance sources are formed between conductive elements of said probe, including said tube sections, which elements are at different potentials, wherein said means for dividing includes said selected gap, and wherein said means for reducing includes said gap being formed with a spacing sufficient to reduce the capacitance of stray capacitors formed from conductive elements on either side thereof to a value substantially below said capacitive difference.

7. Apparatus as claimed in claim 6 wherein the means for reducing further includes means, including said gap, for electrically isolating selected conductive elements from said selected potential, whereby stray capacitances are reduced or eliminated by reducing or eliminating the potential between the corresponding conductive elements.

8. Apparatus as claimed in claim 1 wherein said effective stray capacitance is in the order of 1 pf.

9. A probe for aspirating an ionic liquid sample and for sensing a capacitance difference at the probe tip when it is not in contact with the liquid and when it is in contact with the liquid comprising;
- an aspirating tube of an insulating material extending the length of said probe;
- at least two conductive tube sections coaxial with said aspirating tube, a first of said sections extending from the probe tip, and covering a selected portion of the aspirating tube which is substantially less than all of said aspirating tube, and a second section being spaced by a selected gap from said first section, and covering a portion of said aspirating tube not covered by said first section;
- and means for applying a selected potential to said first section, the selected potential not being applied to the second section, whereby there is a potential difference between said sections.

10. A probe as claimed in claim 9 including a cover tube of an insulating material covering at least the adjacent portions of the first and second sections, the cover tube in conjunction with the aspirating tube maintaining said selected gap.

11. A probe as claimed in claim 9 wherein stray capacitances are formed between conductive elements, including said tube sections, of the probe, which elements are at different potentials; and
- wherein said gap is formed with a spacing sufficient to reduce the capacitance of the stray capacitances formed from conductive elements on either side of the gap to a value substantially below said capacitive difference.

12. A probe as claimed in claim 11 wherein said gap electrically isolates selected conductive elements from said selected potential, whereby at least selected stray capacitances are reduced or eliminated by reducing or eliminating the potential between the corresponding conductive elements.

* * * * *